United States Patent [19]

Curran et al.

[11] 3,932,440

[45] Jan. 13, 1976

[54] P-(1H-TETRAZOL-1-YL)-PHENYLCARBAMATES

[75] Inventors: William Vincent Curran, Pearl River, N.Y.; Andrew Stephen Tomcufcik, Old Tappan, N.J.; Adma Schneller Ross, Suffern, N.Y.

[73] Assignee: American Cyanamid Company, Stamford, Conn.

[22] Filed: June 3, 1974

[21] Appl. No.: 475,478

[52] U.S. Cl. ............................ 260/308 D; 424/269
[51] Int. Cl.² ........................................ C07D 257/04

[58] Field of Search ................................. 260/308 D

[56] References Cited
UNITED STATES PATENTS
3,830,928   8/1974   Mrozik ........................... 260/308 D

*Primary Examiner*—Frederick E. Waddell
*Attorney, Agent, or Firm*—Edward A. Conroy, Jr.

[57] ABSTRACT

This disclosure describes compounds of the class of N-substituted p-(1H-tetrazol-1-yl)phenylthio- or dithio-carbamates useful as antimicrobial agents.

10 Claims, No Drawings

P-(1H-TETRAZOL-1-YL)-PHENYLCARBAMATES

BRIEF SUMMARY OF THE INVENTION

This invention relates to new organic compounds and, more particularly, is concerned with novel 1-phenyl-1H-tetrazoles substituted in the para-position of the phenyl moiety with various sulfur-containing functional groups. The novel compounds of the present invention may be represented by the following general formula:

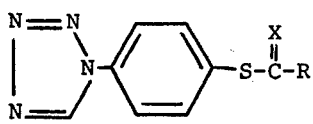

wherein X is divalent oxygen or divalent sulfur and R is methyl, methylamino, dimethylamino, ethylamino, diethylamino, allylamino, or trichloroacetylamino.

DETAILED DESCRIPTION OF THE INVENTION

The novel compounds of the present invention are generally obtainable as white to pale yellow crystalline materials having characteristic melting points and absorption spectra and which may be purified by recrystallization from common organic solvents such as methanol, ethanol, dimethylformamide, acetone, chloroform, ethyl acetate and the like. They are appreciably soluble in non-polar organic solvents such as diethyl ether, benzene, toluene, and the like but are relatively insoluble in water.

Certain of the novel compounds of the present invention may be readily prepared as illustrated by the following reaction scheme:

wherein $R_1$ is methyl or ethyl, $R_2$ is methyl, ethyl, allyl or trichloroacetyl, and X is divalent oxygen or divalent sulfur. In accordance with the above reaction scheme, treatment of p-(1H-tetrazol-1-yl)benzenethiol (I) with an appropriate isocyanate or isothiocyanate provides the corresponding N-monosubstituted thiocarbamate or dithiocarbamate (II). This reaction is best carried out at room temperature in an inert solvent such as methylene chloride or chloroform for a period of time of from about half an hour to a day or more. Treatment of p-(1H-tetrazol-1-yl)benzenethiol (I) with an appropriate dialkyl carbamoyl chloride or thiocarbamoyl chloride provides the corresponding N-disubstituted thiocarbamate or dithiocarbamate (III). This reaction is preferably carried out in dimethylformamide as solvent in the presence of diazabicyclooctane at a temperature of 0°–50°C. for a few hours.

The novel compounds of the present invention are useful as antimicrobial agents and possess broad spectrum activity in vivo against Gram-negative and Gram-positive bacteria. The in vivo antibacterial activity of the novel compounds of the present invention makes them useful as additives to materials which are subject to microbial deterioration such as cutting oils and fuel oils. They are also useful in soaps, shampoos, and topical compositions for the treatment of wounds and burns.

The invention will be described in greater detail in conjunction with the following specific examples.

EXAMPLE 1

Preparation of p-(1H-tetrazol-1-yl)benzenethiol

A mixture of p-aminothiophenol (9.0 g.), sodium azide (7.0 g.), triethyl orthoformate (30 ml.), and

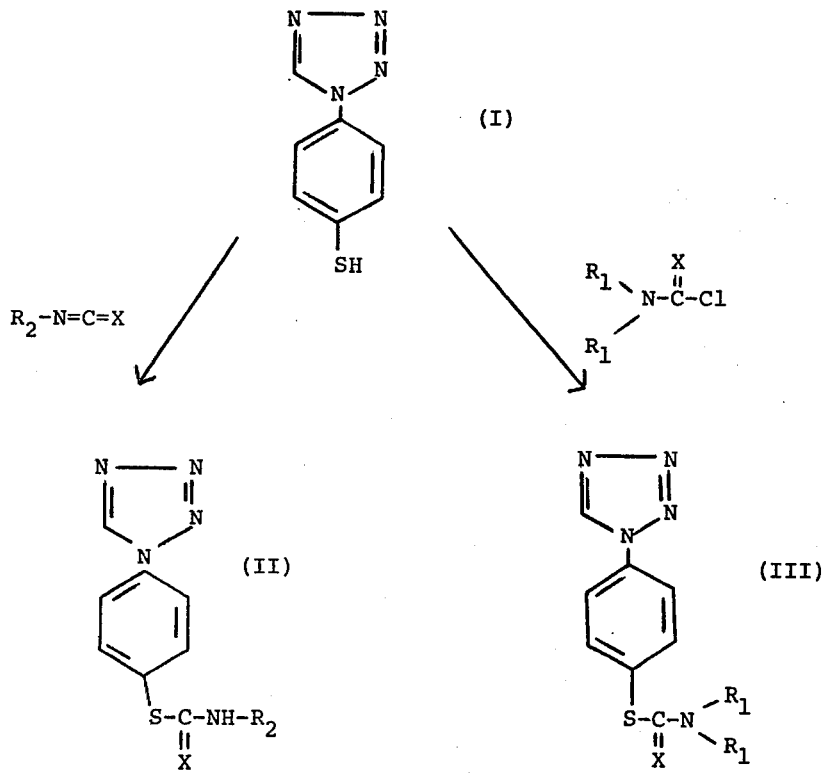

acetic acid (30 ml.) was stirred and heated at 85°C. for 30 minutes. The reaction mixture was evaporated at reduced pressure and diluted with water to give a crystalline product which was collected and recrystallized from chloroform:hexane, m.p. 120°–122°C.

EXAMPLE 2

Preparation of p-(1H-tetrazol-1-yl)phenylmethylthiocarbamate (A)

Methylisocyanate (0.57 g., 10 mmol) was added to a slurry of 1.78 g. (10 mmol) of p-(1H-tetrazol-1-yl)benzenethiol in 15 ml. of methylene chloride. The thick precipitate which formed immediately was filtered off after an hour of stirring to yield white crystals, m.p. 179°–182.5°C. upon recrystallization from ethanol.

EXAMPLE 3

Preparation of p-(1H-tetrazol-1-yl)phenylallyldithiocarbamate (B)

A solution of 1.78 g. of p-(1H-tetrazol-1-yl)benzenethiol and 1.0 g. of allylisothiocyanate in 20 ml. of methylene chloride was stirred at room temperature for 48 hours and filtered to give yellow crystals, m.p. 136°–138°C.

EXAMPLE 4

Preparation of methyldithio p-(1H-tetrazol-1-yl)phenylcarbamate (C)

In a similar manner to Example 3, using methyl isothiocyanate, p-(1H-tetrazol-1-yl)phenylmethyldithiocarbamate was obtained upon recrystallization from ethanol, m.p. 160°–164°C.

EXAMPLE 5

Preparation of p-(1H-tetrazol-1-yl)benzenethiol acetate (D)

A stirred solution of 1.1 g. (6.2 mmol) of p-(1H-tetrazol-1-yl)benzenethiol and 0.8 g. (7.1 mmol) of diazabicyclooctane in 25 ml. of dimethylformamide was cooled in an ice bath and 1.0 ml. (8.2 mmol) of acetyl chloride was added. The mixture was brought to room temperature and stirred 2½ hours. Water was added, and the product was filtered off and recrystallized from ethyl acetate-hexane, m.p. 134°–141.5°C.

In a similar manner but using thioacetyl chloride there was obtained the corresponding p-(1H-tetrazol-1-yl)benzenethiol thioacetate (E).

EXAMPLE 6

Preparation of S-[p-(1H-tetrazol-1-yl)phenyl]trichloroacetylthiocarbamate (F)

Trichloroacetyl isocyanate (1.88 g.) was added dropwise to a solution of 1.78 g. of p-(1H-tetrazol-1-yl)benzenethiol in methylene chloride. In a few minutes a precipitate formed which was filtered after 30 minutes and recrystallized from methylene chloride to give a white crystalline product, m.p. 181°–183.5°C.

EXAMPLE 7

Preparation of dimethylthio p-(1H-tetrazol-1-yl)phenylcarbamate (G)

A mixture of p-(1H-tetrazol-1-yl)benzenethiol (1.1 g.), dimethylcarbamoyl chloride (1.0 ml.), diazabicyclooctane (0.8 g.), and 25 ml. of dimethylformamide was stirred for 1.0 hour in the cold and 1.0 hour at room temperature and then diluted with water (100 ml.) and filtered. The product was recrystallized from ethyl acetate, m.p. 181°–183°C.

EXAMPLE 8

Preparation of diethylthio p-(1H-tetrazol-1-yl)phenylcarbamate (H)

This compound was prepared in a manner similar to the corresponding dimethyl analog of Example 7 using diethylcarbamoyl chloride. The product was recrystallized from ethanol, m.p. 121°–124°C.

EXAMPLE 9

Preparation of dimethyldithio p-(1H-tetrazol-1-yl)phenylcarbamates (I)

This compound was prepared in a manner similar to the corresponding monothio analog of Example 7 using dimethylthiocarbamoyl chloride, m.p. 195°–198°C.

EXAMPLE 10

In vivo activity of the 1-(para-substituted-phenyl)-1H-tetrazoles

The novel compounds of the present invention are active in vivo against a variety of microorganisms. These new antimicrobial agents are thereby potentially useful as therapeutic agents in treating bacterial infections in mammals. The usefulness of these new antimicrobial agents was demonstrated by their ability to control systemic lethal infections in mice in the following test procedure.

The animals used were Carworth Farms CF-1 strain female mice approximately 6 weeks old and averaging 18–22 gm. in weight. Infections were produced by intraperitoneal injections of a 0.5 ml. volume (a lethal dose) of a trypticase soy broth (TSP) dilution (as indicated in Table I) of a 5 hour TSP blood culture of the microorganisms listed in Table I below.

TABLE I

| Microorganism | TSP dilution of a 5 hour TSP culture |
|---|---|
| Proteus mirabilis ATCC 4671 | 1:40 |
| Escherichia coli 311 | $10^{-3}$ |

The test compounds were administered either in a single 0.5 ml. oral tubing dose or by a single 0.5 ml. subcutaneous dose in 0.2% aqueous agar immediately after infection at the indicated dosage levels. The results are set forth in Tables II–III, below, as percent effectiveness (alive/total) at 14 days post infection for each dosage level. The test compounds are identified in Table II–III by the capital letter designation recited in the titles of the preparative examples.

TABLE II

| Oral Dose (mg./kg.) | Percent Effect (Alive/Total) with Escherichia coli 311 | | | |
| --- | --- | --- | --- | --- |
| | (A) | (B) | (C) | (D) |
| 256 | 100(5/5) | | | 40(2/5) |
| 128 | 40(2/5) | 50(1/2) | 0(0/2) | 40(2/5) |
| 64 | 40(2/5) | | | 0(0/5) |
| Oral Dose (mg./kg.) | (F) | (G) | (H) | (I) |
| 256 | | 80(4/5) | 0(0/5) | |
| 128 | 0(0/2) | 20(1/5) | 0(0/5) | 0(0/2) |
| 64 | | 20(1/5) | 0(0/5) | |
| Infected Non-Treated Controls | 2(3/150) | | | |

TABLE III

| Subcutaneous Dose (mg./kg.) | Percent Effect (Alive/Total) with Proteus mirabilis ATCC 4671 | | | |
| --- | --- | --- | --- | --- |
| | (A) | (B) | (C) | (D) |
| 256 | 80(4/5) | 100(5/5) | 80(4/5) | 100(5/5) |
| 128 | 100(5/5) | 40(2/5) | 100(5/5) | 100(5/5) |
| 64 | 80(4/5) | 100(5/5) | 80(4/5) | 0(0/5) |
| Subcutaneous Dose (mg./kg.) | (F) | (G) | (H) | (I) |
| 256 | 100(5/5) | 100(5/5) | 100(5/5) | 60(3/5) |
| 128 | 100(5/5) | 100(5/5) | 80(4/5) | 40(2/5) |
| 64 | 60(3/5) | 60(3/5) | 0(0/5) | 0(0/5) |
| Infected Non-Treated Controls | 9(7/80) | | | |

We claim:

1. A compound of the formula:

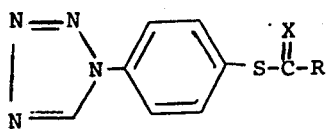

wherein R is a moiety of the formulae:

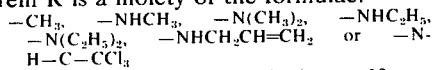

and X is divalent oxygen or divalent sulfur.

2. The compound according to claim 1 wherein X is divalent sulfur and R is methyl.

3. The compound according to claim 1 wherein X is divalent oxygen and R is ethylamino.

4. The compound according to claim 1 wherein X is divalent sulfur and R is ethylamino.

5. The compound according to claim 1 wherein X is divalent sulfur and R is diethylamino.

6. The compound according to claim 1 wherein X is divalent oxygen and R is allylamino.

7. The compound according to claim 1 wherein X is divalent sulfur and R is trichloroacetylamino.

8. The compound according to claim 1 wherein X is divalent oxygen and R is methyl.

9. The compound according to claim 1 wherein X is divalent sulfur and R is methylamino.

10. The compound according to claim 1 wherein X is divalent oxygen and R is dimethylamino.

* * * * *